(12) United States Patent
Palasis

(10) Patent No.: US 6,613,025 B1
(45) Date of Patent: Sep. 2, 2003

(54) METHOD AND APPARATUS FOR DIAGNOSTIC AND THERAPEUTIC AGENT DELIVERY

(75) Inventor: Maria Palasis, Wellesley, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/578,037

(22) Filed: May 25, 2000

(51) Int. Cl.⁷ .............................................. A61M 5/00
(52) U.S. Cl. .................................................. 604/265
(58) Field of Search ........................................ 604/265

(56) References Cited

U.S. PATENT DOCUMENTS

| | | | |
|---|---|---|---|
| 4,346,709 A | 8/1982 | Schmitt | 128/260 |
| 4,846,812 A * | 7/1989 | Walker et al. | 600/581 |
| 5,266,359 A * | 11/1993 | Spielvogel | 427/388.4 |
| 5,620,700 A | 4/1997 | Berggren et al. | 424/435 |
| 5,797,870 A | 8/1998 | March et al. | 604/49 |
| 5,840,059 A | 11/1998 | March et al. | 604/53 |
| 5,846,225 A | 12/1998 | Rosengart et al. | 604/115 |
| 5,911,711 A | 6/1999 | Pelkey | 604/265 |
| 5,954,706 A | 9/1999 | Sahatjian | 604/509 |
| 5,993,972 A * | 11/1999 | Reich et al. | 428/423.1 |
| 5,997,509 A | 12/1999 | Rosengart et al. | 604/164 |
| 5,997,525 A | 12/1999 | March et al. | 604/508 |
| 6,045,565 A | 4/2000 | Ellis et al. | 606/167 |
| 6,162,487 A * | 12/2000 | Darouiche | 424/423 |
| 6,168,580 B1 * | 1/2001 | Yardley | 604/20 |

FOREIGN PATENT DOCUMENTS

| | | | |
|---|---|---|---|
| WO | WO 94/21237 | 9/1994 | A61K/9/22 |
| WO | WO 99/39624 | 8/1999 | |

* cited by examiner

Primary Examiner—J. Casimer Jacyna
(74) Attorney, Agent, or Firm—Kenyon & Kenyon

(57) ABSTRACT

Method and apparatus for diagnostic and therapeutic agent delivery is provided by the present invention. In one embodiment a method for injecting an agent into the body of a patient is provided. This method includes: covering an injection structure having a piercing tip with a coating that contains a first agent; urging the piercing tip of the injection structure into a first target located in the body of the patient; and, maintaining the injection structure in the first target location for a predetermined amount of time. In so doing the agent may be conveniently and accurately delivered to the target site. In another embodiment of the present invention a drug delivery device is provided. This drug delivery device includes a catheter having a proximate end and a distal end and an injection structure coupled to the distal end of the catheter. In this embodiment the catheter is covered with a coating that contains an agent. This coating is adapted to release the agent into the body of a patient after the coating enters the body of the patient; again to conveniently and accurately deliver the agent to the target site.

13 Claims, 6 Drawing Sheets

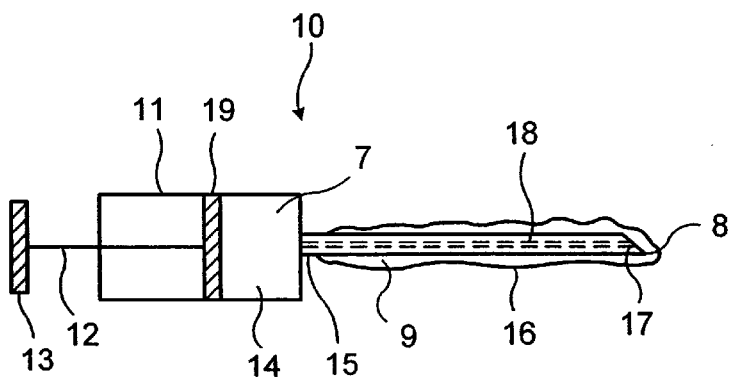
F I G. 1
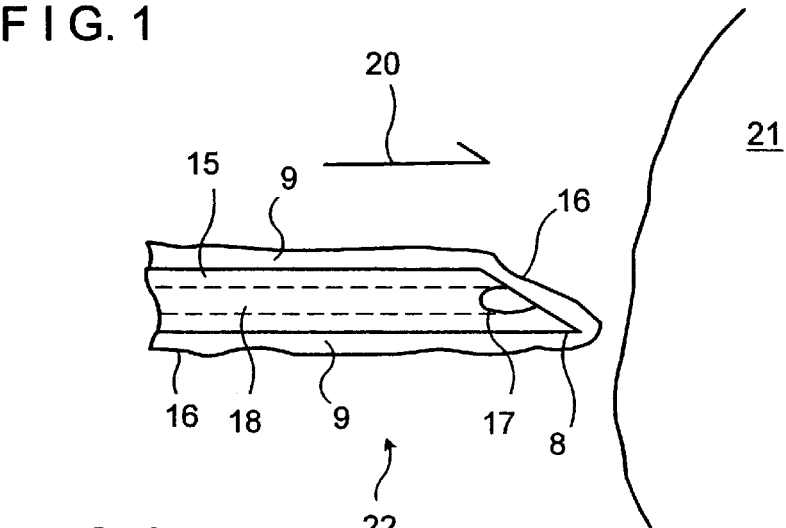
F I G. 2
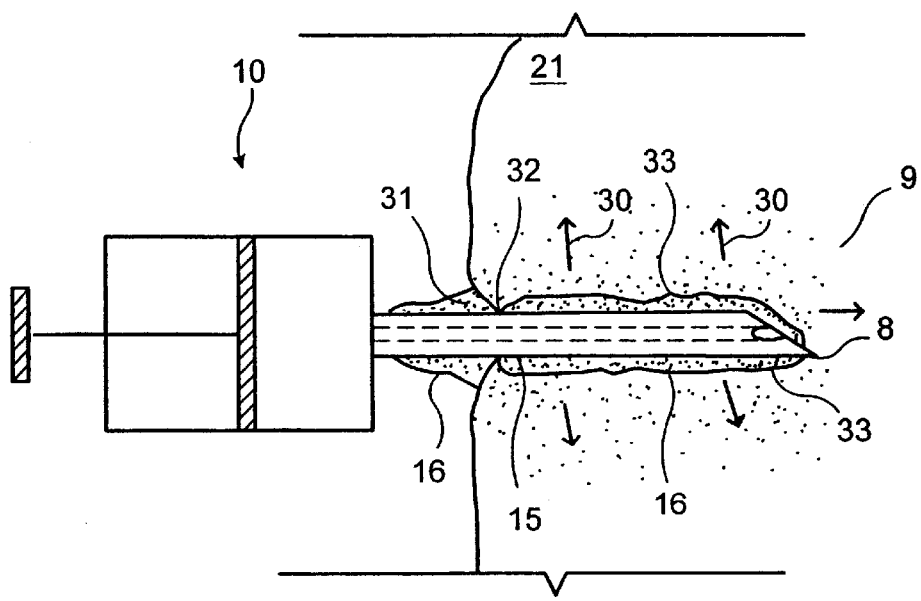
F I G. 3

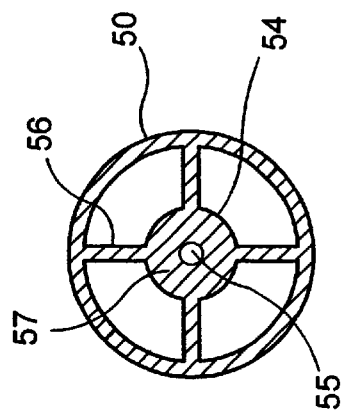
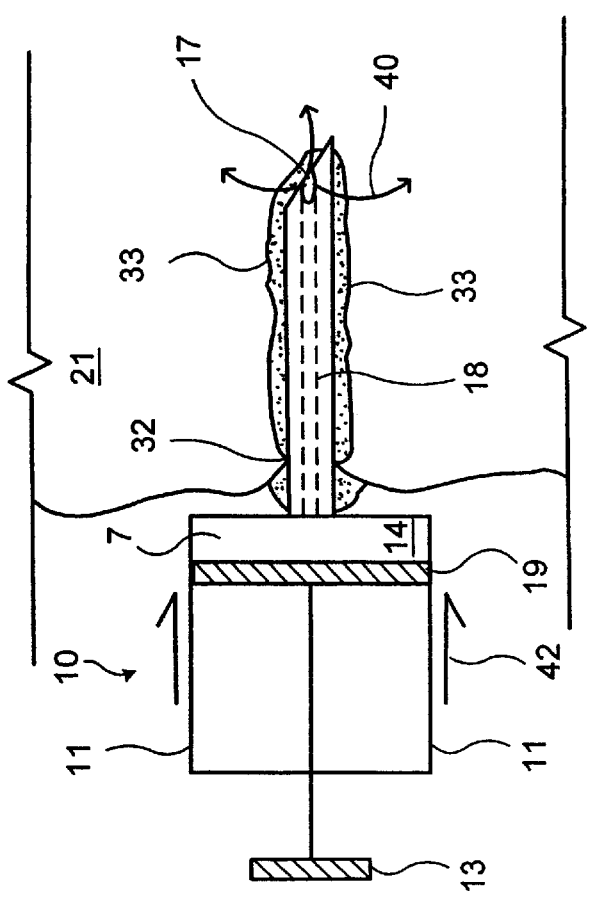
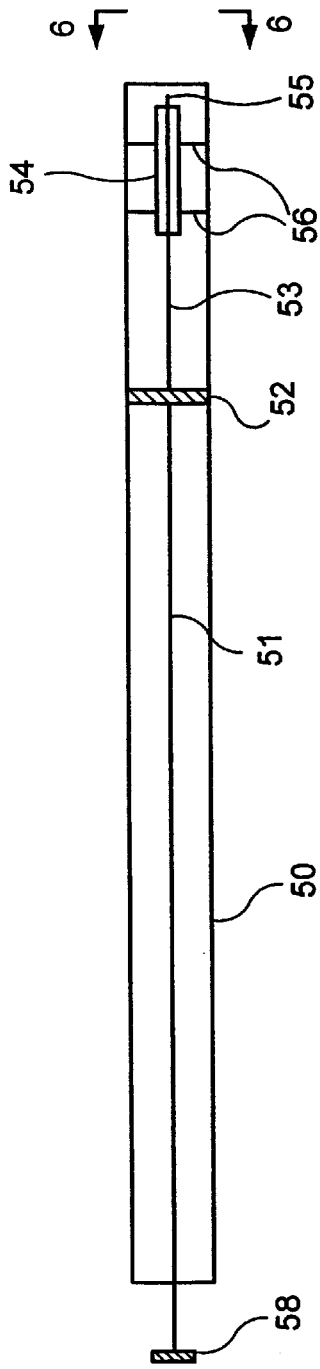
FIG. 6
FIG. 4
FIG. 5

METHOD AND APPARATUS FOR DIAGNOSTIC AND THERAPEUTIC AGENT DELIVERY

FIELD OF THE INVENTION

The present invention regards the delivery of therapeutic and diagnostic agents to a target site of a patient. More particularly the present invention regards method and apparatus for minimizing the amount of backflow or seepage of therapeutic and diagnostic agents from a target site after the agent has been delivered to the target site.

BACKGROUND OF THE INVENTION

Accurate and reliable delivery of therapeutic and diagnostic agents is required for the successful execution of numerous medical procedures. In the past, however, the accurate and reliable delivery of these agents during a medical procedure was not always plausible. For example, when a syringe is utilized to deliver an agent to a target site within the body some, if not all, of the injected agent may passively drain from the target site after the needle of the syringe is removed from the target site. This undesirable drainage is accentuated when the target site is an active muscle such as the heart. Here, the agent would not only passively drain from the open channel created by the removal of the needle, it would also be actively forced from the open channel during each muscular contraction.

The drainage of these agents after their injection into the body is problematic for several reasons. First, when a portion of the agent drains away from the injection site it is no longer available to treat the target site and is, consequently, wasted. Moreover, when the agent drains from the target site, but still remains within the body, the agent can interact with and effect other sites within the body of the patient. This unwanted contact and interaction can lead to complications and unpredictable results. In addition, the untimely drainage of the agent from the targeted site may render the agent ineffective because the agent did not remain in contact with the targeted site for the requisite interaction time. Consequently, the agent would need to be reintroduced to the target site through a second procedure. In sum, the uncontrolled drainage of an agent from a targeted site of the body is an objectionable occurrence.

Some conventional processes seek to address this problem. In one known process an erodible polymer is utilized to deliver the drug to a targeted site over a long period of time. In this known process the erodible polymers are blended with a drug and then deposited at the targeted site requiring their use. Over time, the polymer will slowly erode and, concomitantly, delivery the drug to its surrounding area. However, when the targeted site is not readily accessible in the body, substantial operative procedures may be required to properly position the polymer within the body. In addition, when the drug needs to be delivered over a short period of time, the polymer can erode too quickly, allowing the premature drainage of drug. Likewise, if the drug is to be delivered for an extended period of time, the polymer may not erode quickly enough and the drug will be delivered over an unacceptably long time frame.

Accordingly, in view of the potential drawbacks of conventional drug delivery techniques, there exists a need for a method and device that provide for the controlled, localized delivery of agents to target locations in the body which avoid the unwanted shortcomings encountered in the past.

SUMMARY OF THE INVENTION

Method and apparatus for diagnostic and therapeutic agent delivery is provided by the present invention. In one embodiment a method for injecting an agent into the body of a patient is provided. This method includes: covering an injection structure having a piercing tip with a coating that contains a first agent; urging the piercing tip of the injection structure into a first targeted site located in the body of the patient; and, maintaining the injection structure in the first targeted site location for a predetermined amount of time. In so doing the agent may be conveniently and accurately delivered to the target site.

In another embodiment of the present invention a drug delivery device is provided. This drug delivery device includes a catheter having a proximate end and a distal end and an injection structure coupled to the distal end of the catheter. In this embodiment the injection structure is covered with a coating that contains an agent. This coating is adapted to release the agent into the body of a patient after the coating enters the body of the patient; again to conveniently and accurately deliver the agent to the target site.

BRIEF DESCRIPTION OF THE DRAWINGS

FIG. 1 is a side view of a delivery device in accordance with a first embodiment of the present invention.

FIG. 2 is an enlarged view of the distal end of the delivery device of FIG. 1 positioned near a target site.

FIG. 3 is a side view of the delivery device of FIG. 1 after it has entered the target site.

FIG. 4 is a side view of the delivery device of FIG. 1 positioned within the target site after the plunger of the delivery device has been partially depressed.

FIG. 5 is a side view of a catheter in accordance with a second embodiment of the present invention.

FIG. 6 is an end view of the catheter taken along line 6—6 of FIG. 5.

DETAILED DESCRIPTION

Figure 7:
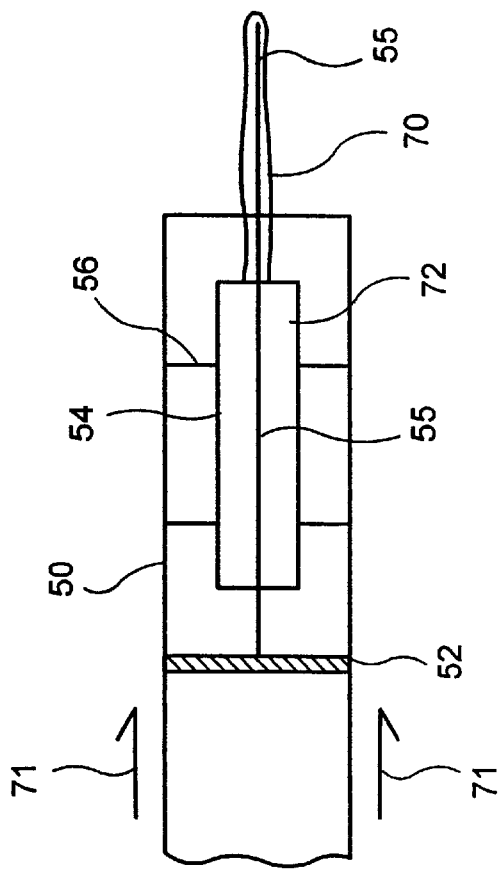
FIG. 7 is an enlarged view of the distal end of the catheter from FIG. 5 with the injection structure shown protruding from the distal end of the catheter.

FIG. 1 is a side view of a delivery device 10 in accordance with a first embodiment of the present invention. The delivery device 10 in this first embodiment has an injection structure 15 rigidly and perpendicularly coupled to a storage reservoir 11. The storage reservoir 11 may be tube shaped and may have a circular cross-section. Slidably mounted within the storage reservoir 11 is a rigid disc 19 which defines a chamber 7 in the distal end of the storage reservoir 11. A rigid connector 12 is perpendicularly connected to the disc 19 and to a handle 13 located outside the storage reservoir 11. This connector 12 connects the disc 19 with the handle 13 such that when the handle 13 is moved the disc 19 is concomitantly slid within the storage reservoir 11, reducing the volume of the chamber 7 and, thereby, forcing any contents of the chamber 7 through the lumen 18 of the injection structure 15 and out the orifice 17 located at the distal end of the injection structure 15. The distal end of the injection structure 15, which may have a circular cross-sectional profile in this first embodiment, also has a piercing tip 8 at its distal end. This piercing tip 8 may have a sharp point designed to puncture into soft tissue, hard tissue or bone.

The storage reservoir 11, handle 13, connector 12, and disc 19 may be made from plastic, metal, a combination thereof or some other suitable material. Likewise, the injection structure 15 may also be made from plastic, metal, a combination thereof or some other suitable material. For example, in this first embodiment, in order to maintain a sharp and resilient piercing tip 8, the injection structure 15 may be made from a rigid plastic while the piercing tip 8 may be made from a surgical metal alloy.

Also evident in FIG. 1 is a coating 16, which, as can be seen, may cover a large portion of the injection structure 15. In this first embodiment a first agent 9 is contained by the coating, through absorption by the coating. The first agent may also be contained by the coating 16 through adsorption or any other means. A second agent 14 may be located within the chamber 7. The first agent 9 may be a therapeutic, a diagnostic or any other suitable agent and the second agent 14 may be an uptake agent, an anti-inflammatory agent, an anesthetic or, likewise, any other suitable agent. These first and second agents may work alone to produce independent results; they may also work together to produce cumulatively beneficial results. The injection structure 15 of the delivery device 10 may be used to deliver the first agent 9, which is located in the coating 16, to a target site (not shown) of a patient.

In use, the delivery device 10 may be first positioned near the target site by known percutaneous or endoluminal techniques which manipulate the device through blood vessels or other lumens and cavities within the body. Then, after being properly positioned near the target site, the injection structure may be urged into the target site of the patient, thereby creating an injection channel defined by the outer surface of the coating 16. The injection structure 15 may then remain within the target site until the proper dosage of the first agent 9 has been delivered to the target site from the coating 16. The length of time required to deliver the requisite dosage will depend upon many factors including the agent being delivered and the composition of the target site; it can be a few seconds to several minutes or 40 more. During this time, as required by the specific circumstances of the procedure, a second agent 14, resident within the chamber 7, may or may not be introduced into the target site. This second agent 14, which, as noted above, may be an anti-inflammatory, an uptake agent, or any other type of agent, may be introduced into the target site by depressing the handle 13 and ultimately urging the second agent 14 from the orifice 17. Then, after the requisite agent or agents have been deployed and the necessary time has passed, allowing the agent or agents to interact with each other and the target site, the injection structure 15 may be removed from the target site.

Organs and tissues that may be treated by the method of the present invention include any mammalian tissue or organ, whether injected in vivo or ex vivo. Specific, non-limiting examples include heart, lung, brain, liver, skeletal muscle, smooth muscle, kidney, bladder, intestines, stomach, pancreas, ovary, prostate, eye, tumors, cartilage, and bone.

The therapeutic agents deployed may be used in any application including the treating, preventing or otherwise affecting the course of a disease, tissue or organ dysfunction. For example, the methods of the invention can be used, as desired, to induce or inhibit angiogenesis to prevent or treat restenosis, to treat a cardiomyopathy or other dysfunction of the heart, for treating Parkinson's disease, a stroke or other dysfunction of the brain, for treating cystic fibrosis or other dysfunction of the lung, for treating or inhibiting malignant cell proliferation, for treating any malignancy, and for inducing nerve, blood vessel or tissue regeneration in a particular tissue or organ.

FIG. 2 is an enlarged side view of the distal end 22 of the injection structure 15 from FIG. 1. In FIG. 2 the target site 21 to be pierced is clearly shown. This target site 21 may be an organ or a hard or soft tissue location within the patient, including the heart, bladder, liver, prostate, as well as a growth or tumor situated within the body of a patient. Also evident in FIG. 2 is the injection structure 15, the lumen 18 within the injection structure 15, the orifice 17 near the piercing tip 8 of the injection structure 15, and the coating 16 which contains the first agent 9. The arrow 20 of FIG. 2 indicates a preferred direction of movement of the injection structure 15 towards the target site 21.

FIG. 3 is a side view of the delivery device 10 from FIG. 1 after it has entered the target site 21. As can be seen the injection structure 15 has created an injection channel 33 defined by the outer surface of the coating 16. As can also be seen the coating 16 may become pushed away from the point of the piercing tip 8 and has also mounded up near the point of entry 32 of the injection structure 15 in the target site 21, depending upon the coating materials used. The coating 16 has been displaced in this manner due to the opposing frictional resistance of the target site 21 against the injection structure 15 during the injection of the injection structure 15 into the target site 21. Once the injection structure 15 and the coating 16 have entered the target site 21 the first agent 9, resident in the coating 16, may diffuse into the surrounding tissue. The diffusion of the first agent 9 into the surrounding target site 21 is depicted with arrows 30 in FIG. 3.

The coating 16 and the first agent 9 described above may be applied to the injection structure 15 at various times and in various ways. For example, they may be applied prior to the medical procedure and during the manufacturing process. They may also be spread onto the injection structure 15 contemporaneous with the medical procedure being performed, by dipping the injection structure into a container containing the coating. When the coating is placed by the manufacturer onto the device, the injection structure 15 may be covered with a sheath or some other material to prevent the premature removal of the coating 16 or the first agent 9 from the injection structure 15. Alternatively, the coating and the agent may be applied to the rigid structure at different times. For example, the coating may be applied by the manufacturer during the manufacture of the device while the agent may be applied by the operator contemporaneous with the procedure.

FIG. 4 is a side view of the injection device 10 wherein the second agent 14, resident in the chamber 7, is being forced through the orifice 17 into the target site 21. As noted above, this second agent 14 may be utilized to increase the cellular uptake of the first agent 9 into the target site 21 and, accordingly, may also be used to reduce the amount of time required to leave the injection structure 15 in the injection channel 33. FIG. 4 illustrates the second agent exiting the orifice 17 with arrows 40 and also indicates the directional movement of the disc 19, with arrows 42, as it is used to urge the second agent 14 out the orifice 17. In other embodiments, the orifice 17 may be located in alternative positions such as the side of the injection structure; moreover, several orifices rather than only one may be located at various locations in the injection structure.

The first agent 9 resident within the coating to be delivered to the target site may be, among other things, a therapeutic, a tracer material, and a diagnostic agent. The therapeutic may include therapeutic agents such as pharmaceutically active compounds, proteins, cells, oligonucleotides, ribozymes, anti-sense oligonucleotides, DNA compacting agents, gene/vector systems (i.e., any vehicle that allows for the uptake and expression of nucleic acids), nucleic acids (including, for example, recombinant nucleic acids; naked DNA, cDNA, RNA; genomic DNA, cDNA or RNA in a non-infectious vector or in a viral vector and which further may have attached peptide targeting sequences; antisense nucleic acid (RNA or DNA); DNA chimeras which include gene sequences and encoding for ferry proteins such as membrane translocating sequences ("MTS") and herpes simplex virus-1 ("VP22")); viral liposomes; cationic and anionic polymers; and, neutral polymers that are selected from a number of types depending on the desired application.

Non-limiting examples of virus vectors or vectors derived from viral sources include adenoviral vectors, herpes simplex vectors, papilloma vectors, adeno-associated vectors, retroviral vectors, and the like.

Non-limiting examples of biologically active solutes include: anti-thrombogenic agents such as heparin, heparin derivatives, urokinase, and PPACK (dextrophenylalanine proline arginine chloromethylketone); antioxidants such as probucol and retinoic acid; angiogenic and anti-angiogenic agents and factors; agents blocking smooth muscle cell proliferation such as rapamycin, angiopeptin, and monoclonal antibodies capable of blocking smooth muscle cell proliferation; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic/antiproliferative/anti-mitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; antimicrobials such as to triclosan, cephalosporins, aminoglycosides, and nitorfurantoin; anesthetic agents such as lidocaine, bupivacaine, and ropivacaine; nitric oxide (NO) donors such as lisidomine, molsidomine, L-arginine, NO-protein adducts, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warafin sodium, Dicumarol, aspirin, prostaglandin inhibitors, platelet inhibitors and tick antiplatelet factors; vascular cell growth promotors such as growth factors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogeneus vascoactive mechanisms; survival genes which protect against cell death, such as anti-apoptotic Bcl-2 family factors and Akt kinase; and combinations thereof. Cells can be of human origin (autologous or allogenic) or from an animal source (xenogeneic), genetically engineered if desired to deliver proteins of interest at the injection site. The delivery mediated is formulated as needed to maintain cell function and viability, and modifications are routinely made by one skilled in the art.

Polynucleotide sequences useful as an agent in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides of the invention can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body. In addition, the polypeptides or proteins that can be utilized, or whose DNA can be incorporated, include without limitation, angiogenic factors and other molecules competent to induce angiogenesis, including acidic and basic fibroblast growth factors, vascular endothelial growth factor, hif-1, epidermal growth factor, transforming growth factor $\alpha$ and $\beta$, platelet-derived endothelial growth factor, platelet-derived growth factor, tumor necrosis factor $\alpha$, hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof.

Still other useful factors, which can be provided as polypeptides or as DNA encoding these polypeptides, include monocyte chemoattractant protein ("MCP-1"), and the family of bone morphogenic proteins ("BMP's"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

Examples of the diagnostic agents useful for the practice of the present invention include: Corticotropin, Cosyntropin, Benzylpenicilloyl-Polylysine, Candida Albicans, Histoplasmin, Sincalide, Lactose, Indigotindisulfonate, Mannitol, Edrophonium, Neostigmine, Arginine, Ditrizoate Meglumine, Diatrizoate Sodium, Gadopentetate, Iodixanol, Iohexol, Tuberculin, Fluorescein Sodium, Fluorexon, Histamine, Isosulfan Blue, Methacholine, Rose Bengal, and Fluorescein Sodium.

The coating discussed herein may be one of several commercially available materials. Further to the above, it may be a swellable porous polymer used to absorb a volume of concentrated agent that, when placed within the target site, facilitates the diffusion of the first agent into the target site according to a known concentration and diffusion gradient. Alternatively, the coating may be a charged polymer which may adsorb high concentrations of oppositely charged agent, and, then, may release the agent upon contact of the polymer with the target site. Moreover, the polymer may also have properties which allow it to shrink or change ionic character, thereby facilitating the release of the agent from the coating in response to an environmental stimuli such as pH, ionic strength of the target site, pressure, and temperature. For example, if the therapeutic agent is dissolved in the polymer at a certain pH, the swollen polymer will then shrink when placed into the tissue at a different physiological pH. Alternatively, the release of the first agent could be triggered by the second agent 14, located within the chamber 7. In this case, the uptake agent 14 or triggering solution would be a buffer or salt solution which would be delivered through the lumen while the injection structure 15 was resident within the target site 21. Then, after coming in contact both with the target site 21 and the polymer containing the agent, the uptake agent 14 would facilitate the diffusion of the agent into the target site 21. Moreover, as discussed below, rather than remaining on the injection structure, the polymer may also be released from the injection structure and remain within the body after the injection structure is removed.

Specific suitable biocompatible polymers for use in the present invention include, but are not limited to, polycarboxylic acids, cellulosic polymers, including cellulose acetate and cellulose nitrate, gelatin, polyvinylpyrrolidone, cross-linked polyvinylpyrrolidone, hydrogels, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, ethylene vinylacetate, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof as well as other biodegradable, bioabsorbable and biostable polymers and copolymers.

Like the various coatings and first agents listed above various second agents may also be utilized in the present invention. For example, certain detergents, polymers (polyvinyl pyrrolidone SP 1017 (Supratek Pharma), protamine sulfate, and polysine), and drugs (anti-inflammatory, anti-apoptotic, angiogenic and vessel stabilizing) may be injected into the target site to improve the effectiveness of the present invention.

A second embodiment of the present invention is illustrated in FIG. 5. As can be seen, the catheter 50 in FIG. 5 contains: a push rod 51 centrally located within the catheter 50; a disk 52 slidably movable within the catheter 50 and rigidly coupled to the push rod 51; a tubular injection structure 53 also located within the catheter 50 and rigidly coupled to the disk 52; supports 56, supporting the dispensing chamber 54 in the center of the circular catheter 50; and, a piercing tip 55 located at the distal end of the injection structure 53. Like the delivery device 10 above, catheter 50 may also be used to deliver agents to a target site within the body.

FIG. 6 is a view taken from line 6—6 of FIG. 5. As can be seen in FIG. 6, the catheter 50 in this embodiment has a substantially circular cross-section, supports 56 support the dispensing chamber 54 in the center of the catheter 50, and dispensing chamber 54, has a circular cross-section and an opening 57 at its distal end. This opening 57, allows the piercing tip 55 of the injection structure 53 (not shown in this figure) to exit the dispensing chamber 54 with a coating of polymer surrounding it. In other words, the exit orifice 57, of the dispensing chamber 54 is sized to act as a squeegee which passes a predetermined amount of polymer stored within the dispensing chamber 54 onto the injection structure 53 as the injection structure 53 is pushed through and emerges from the dispensing chamber 54. Alternatively, the dispensing chamber could contain the first agent which may be absorbed onto the polymer resident on the injection structure when the injection structure was retracted into the dispensing chamber. In this alternative embodiment, the dispensing chamber would contain the first agent, but not necessarily the polymer.

In use, an operator would position the distal end of the catheter 50 near the target site (not shown). Next, the injection structure 53 would be pushed through the dispensing chamber 54 containing a polymer and a first agent in order to first coat the injection structure 53 and then to pierce into the targeted site. The injection structure would continue to be pushed through the dispensing chamber 54 and into the target site until the requisite amount of the injection structure 53 had entered the target site. Then, after keeping the injection structure in the targeted site of the body until the first agent had diffused into the targeted site of the body, the operator would extract the injection structure 53 from the target site and the injection channel by pulling on the handle 58 or, alternatively, by pulling on the proximate end of the catheter.

This coating and injection procedure may be repeated for the same injection channel by pushing the handle 58 and again driving the injection structure 53 through the dispensing chamber 54 and into the target site. Alternatively, the procedure may be repeated for a different targeted site by repositioning the distal end of the catheter 50 and then by driving the injection structure 53 through the dispensing chamber 54 into the new target site. In either case, the procedure may be repeated until the requisite amount of first agent has been administered or until the contents of the dispensing chamber have been depleted. When additional agent needs to be delivered to the target site, but the contents of the dispensing chamber 54 have been depleted, the catheter 50 may be disposed of and a new one may be used. Alternatively, a new dispensing chamber 54 may be inserted into the distal end of the catheter 50 or the existing dispensing chamber may be refilled.

FIG. 7 is an enlarged view of the distal end of the catheter 50 from FIG. 5. In FIG. 7, the disk 52 has been slid closer to the distal end of the catheter 50 as indicated by arrows 71 and, the injection structure 53, which has been coated with the polymer 70, now protrudes from the end of the catheter 50.

In use and as described above, the injection structure 53 may be slid through the dispensing chamber 53 and directly into the target site. Alternatively, the catheter may be positioned away from the target site when the injection structure 53 is slid through the dispensing chamber 54 to load the polymer 70. Then, as required, the injection structure, now protruding from the distal end of the catheter 50, may be inserted directly into the target site. An advantage of loading the polymer 70 onto the injection structure 53 prior to positioning the catheter near the target site is that the injection structure 53, protruding from the distal end of the catheter 50, may be used to assist in the positioning of the catheter 50 near the target site.

Figure 8:
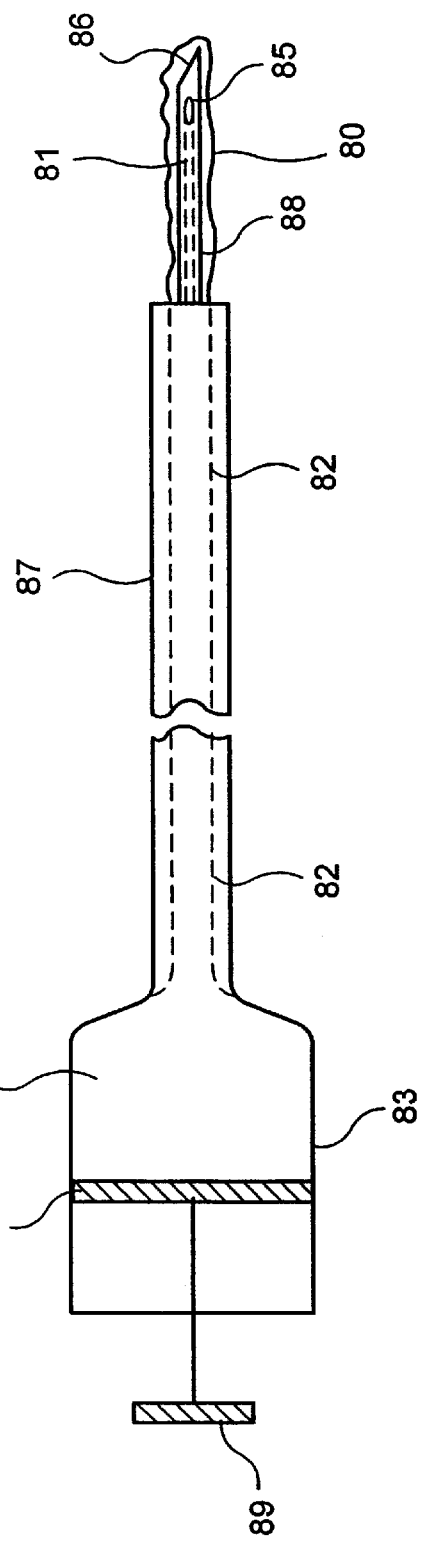
FIG. 8 is a side view of a catheter in accordance with a third embodiment of the present invention.

FIG. 8 is a side view of a third embodiment of the present invention. In FIG. 8, a handle 89 is rigidly connected to a circular sliding disc 891 which is in contact with a storage reservoir 83 which may contain an uptake agent 84. The storage reservoir 83 is connected to and is in fluid communication with a tube 82 located within the catheter 87. The tube 82 connects the storage reservoir 83 with the lumen 81 of the syringe 88. The tube 82, like the catheter 87 and the storage reservoir 83, may be circular and may be made from a surgical grade polymer.

The needle 88 of FIG. 8 is rigidly coupled to the distal end of the tube 82. The needle 88 contains an orifice 85 which is in communication with the lumen 81 and is located on the side of the needle. The needle 88 also contains a piercing tip 86 at its distal end. This piercing tip may be made from various rigid and hard materials such as iron, steel, or other surgical grade alloys and should be configured to permit it to puncture into targeted tissue sites located within the body of the patient.

As is evident in FIG. 8, the needle 88 has been pretreated with a polymer 80 and is consequently ready for use. As described above, the piercing tip 86 of the needle 88 will first be positioned adjacent to a target site. Next, the operator will push the needle 88 into the target site and support the needle 88 within the target site for a predetermined amount of time. If required, after the needle 88 has entered the target site, thereby creating the injection channel within the target site, the uptake agent 84, resident within the storage reservoir 83, may be squeezed from the storage reservoir 83, urged through the tube 82, into the lumen 81, and out the orifice 85. As noted above, this uptake agent may be used to reduce the amount of time required to deliver the agent to the target site or for other purposes such as inflamation reduction and anesthetic delivery. After the agent in the coating has been properly delivered the needle may be removed from the target site.

Figure 9:
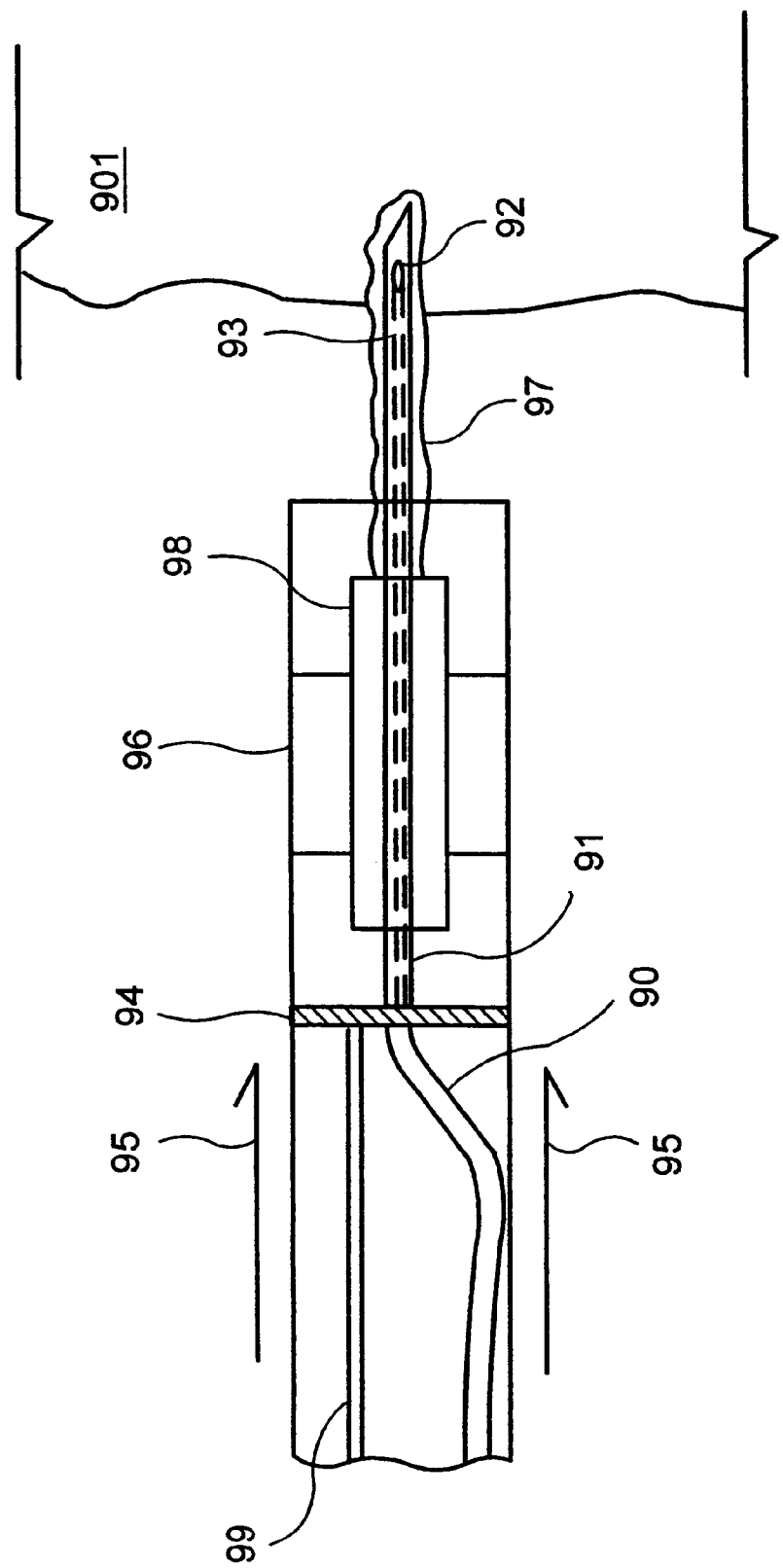
FIG. 9 is an enlarged view of the distal end of a catheter in accordance with a fourth embodiment of the present invention.

FIG. 9 is an enlarged view of the distal end of a catheter 96 in accordance with a fourth embodiment of the present invention. Arrows 95 in this embodiment illustrate the direction of movement of the disk 94 within the catheter 96. As is evident, a flexible tube 90 may be coupled to one side of the disk 94 and a needle 91 may be coupled to the other side of the disc 94. The flexible tube 90 and the needle 91 may be in fluid communication with each other through the disk 94. The flexible tube 90 connects the disk 94 with a storage reservoir (not shown). This flexible tube 90 is sized to connect the disc 94 with the storage reservoir when the disc 94 has been slid to its furthest point from the storage reservoir. Consequently, as is evident in FIG. 9, the flexible tube 90 will sag within the catheter 96 when the disc 94 is not positioned at its furthest point from the storage reservoir.

The distal end of the catheter in FIG. 9 also contains an orifice 92 located near the distal end of the needle 91. This orifice 92 may be in fluid communication with the lumen 93 located within the needle 91 which may be in turn in fluid communication with the flexible tube 90.

In use, when required during the procedure, the operator can push the handle (not shown) connected to the pushrod 99 to slide the disc 94 towards the distal end of the catheter 96. As the disc is slid, the needle 91, coupled to the disc 94, will be pushed through the dispensing chamber 98 out the distal end of the catheter 96 and into the target site 901 of the patient. The needle will remain there for a predetermined amount of time dependent upon the agent being delivered from the polymer and the properties of the target site. If required, and as discussed above, an uptake agent may be delivered through the flexible tube 90 and out the orifice 92 of needle 91 into the targeted site. Then, upon the completion of the procedure, the needle 91 would be removed from the targeted site.

Figure 10:
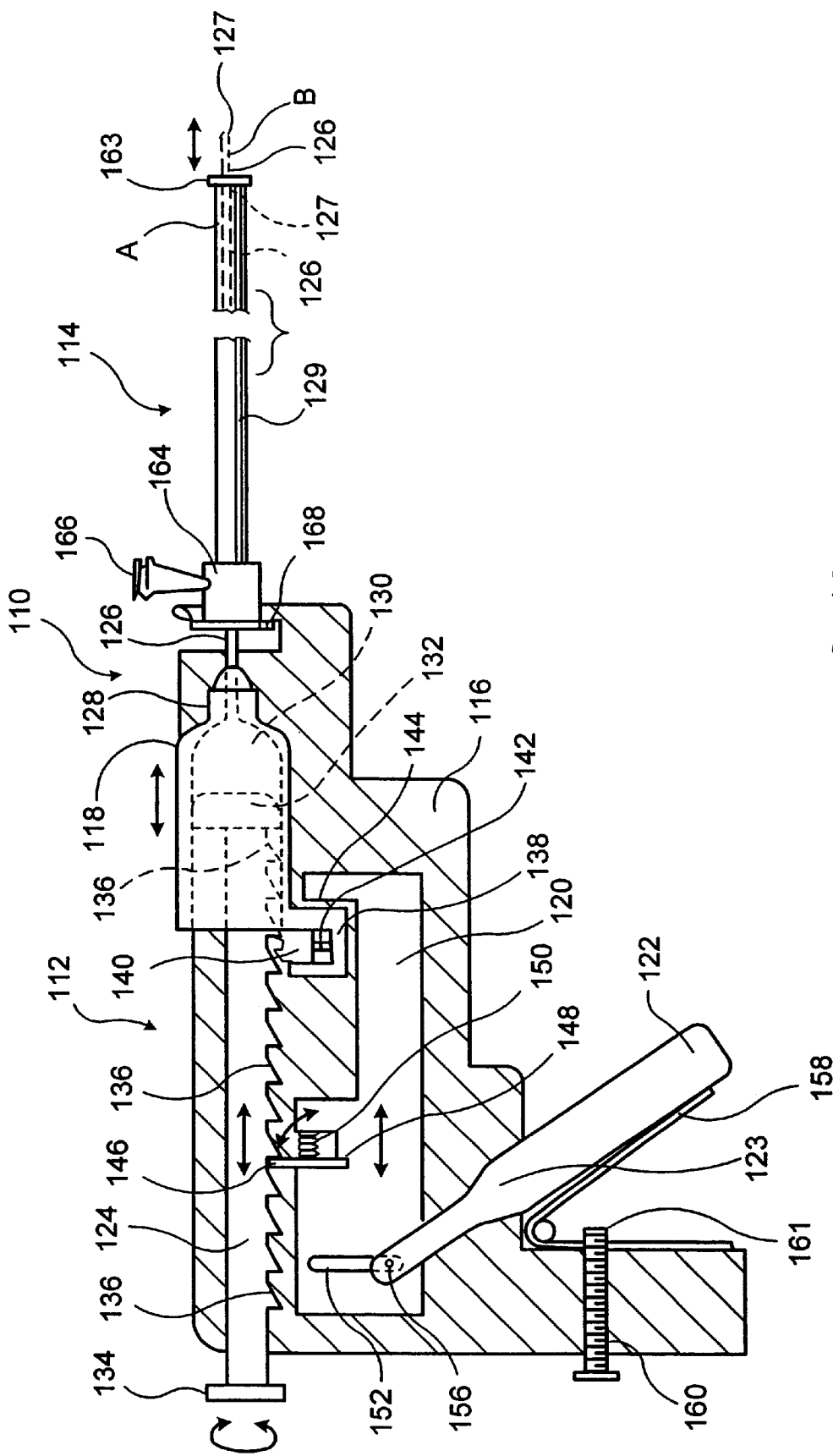
FIG. 10 is a side cross-sectional view of an injection catheter in accordance with a fifth embodiment of the present invention.

FIG. 10 is a side view of a fifth and preferred embodiment of the present invention, which uses a PMR catheter assembly 110 including a dosage actuator gun 112 and catheter 14. In this embodiment, gun 112 includes a body 116. Slidably disposed within body 116 and schematically shown in FIG. 10 is a syringe 118, slider body 120 and plunger 124. Syringe 118, slider body 120 and plunger 124 are slidable proximally and distally as shown by the arrows adjacent these respective elements. Trigger 122 is pivotally connected about pin 123 to body 116. It can be appreciated that those skilled in the art of mechanical design could readily fashion a gun 112 based on the schematic description herein.

Catheter 114 includes an inner tubular shaft 126. Inner tubular shaft 126 includes a sharpened distal end 127. Like syringe 118, slider 120 and plunger 124, inner shaft 126 can be moved proximally or distally as shown by the arrows. More particularly, inner shaft 126 can be moved from a proximal position A wherein tip 127 is disposed within an outer shaft 129 of catheter 114 to a second position B, wherein tip 127 is disposed distally of outer shaft 129.

Syringe 118 includes an inner chamber 130 for containing a dosage of a drug or other fluid. Disposed at the distal end of plunger 124 is a plunger seal 132. Syringe 118 including plunger seal 132 preferably are packaged to contain a second agent prior to placement in gun 112. Syringe 118 includes a Luer fitting 128 or similar attachment device to fluidly connect inner shaft 126 to syringe 118. The proximal ends of plunger 124 includes a handle 134. Handle 134 can be used to rotate plunger 124 about its longitudinal axis within housing 116. Plunger 124 includes a plurality of teeth 136 extending therefrom. Syringe 118 also includes a cradle 138 in which is disposed a one-way plunger lock 140 which is biased toward plunger 124 by spring 142. Lock 140 includes one or more teeth having a slope which allows teeth 136 of plunger 124 to be advanced distally thereover, but engages with teeth 136 to prevent plunger 124 from being withdrawn proximally. Plunger 124 can, however, be withdrawn proximally if it is rotated about its longitudinal axis by using handle 134 such that teeth 136 are disposed away from lock 140, for example, pointed upward rather than downward as shown in FIG. 10.

Slider 120 includes a syringe restraint member 144 which includes a surface engageable with cradle 138 of syringe 118. A plunger advancing member 146 is pivotally attached to slider 120 by pin 148. A spring 150 biases advancing member 146 toward a vertical position as shown in FIG. 10. As slider 120 moves proximally relative to plunger 124, advancing member 146 pivots downwardly as shown by the arrow allowing slider 120 to move proximally relative to plunger 124. Advancing member 146, however, will pivot back to the vertical position after passing over a tooth 136 and be braced in the vertical position by slider 120 to engage the vertical proximal side of one of the teeth 136. Slider 120 includes a slot 152. A pin 156 extends through an end of trigger 122 and is slidable within slot 152. A spring 158 biases trigger 122 into the position shown. Trigger 122 is, however, pivotable in the direction shown by the arrow about pin 123 between the position shown and an adjustment screw 160. Adjustment screw 160 has a distal end 161 which is engageable with trigger 122 to limit the pivoting of trigger 122 in a clockwise direction about pin 123.

Catheter 114 includes a preferably radiopaque, atraumatic hood 163 at its distal end and a manifold 164 at its proximal end. Manifold 164 includes a port 166 for infusion or withdrawal of fluids from catheter 114 through a lumen defined between inner shaft 126 and outer shaft 129. Manifold 164 also includes a flange 168 engageable with a portion of body 116 to connect body 116 to catheter 114.

Figure 11:
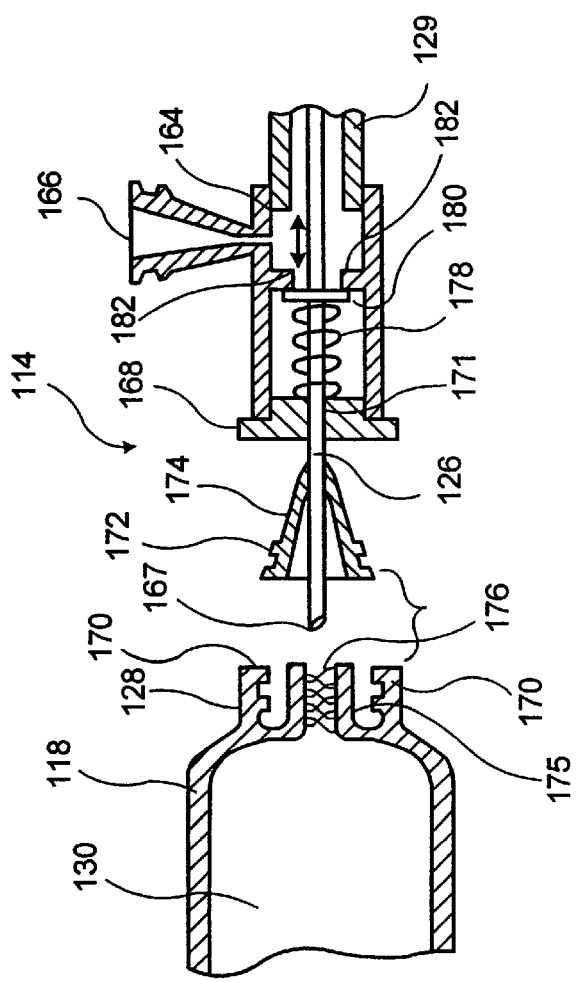
FIG. 11 is an enlarged cross-sectional view of the connection point between the catheter and the activator gun of FIG. 10.

FIG. 11 is a cross-sectional view of a portion of the catheter assembly 110 including a portion of catheter 114 including syringe 118. Luer fitting 128 includes a threaded portion 170 engageable with a threaded portion of a compatible Luer fitting 174 connected to inner shaft 126. Syringe 118 defines an inner shaft receiving lumen 175 sealed with polymer or rubber seal 176 which can be punctured by a sharpened distal end 167 of inner shaft 126 when threads 172 are advanced into threads 170. A fluid connection thus results between the lumen through inner shaft 126 and chamber 130. Flange 168 can be part of a seal 171 which creates a substantially fluid tight seal between inner shaft 126 and manifold 164 while allowing inner shaft 126 to move proximally and distally in the direction as shown by the arrow within manifold 164 of outer shaft 129. A spring 178 biases inner shaft 126 distally relative to manifold 164 and outer shaft 129. The travel of inner shaft 126 distally is limited by engagement of a stop disc 180 with stop ring 182 of manifold 164.

Figure 12:
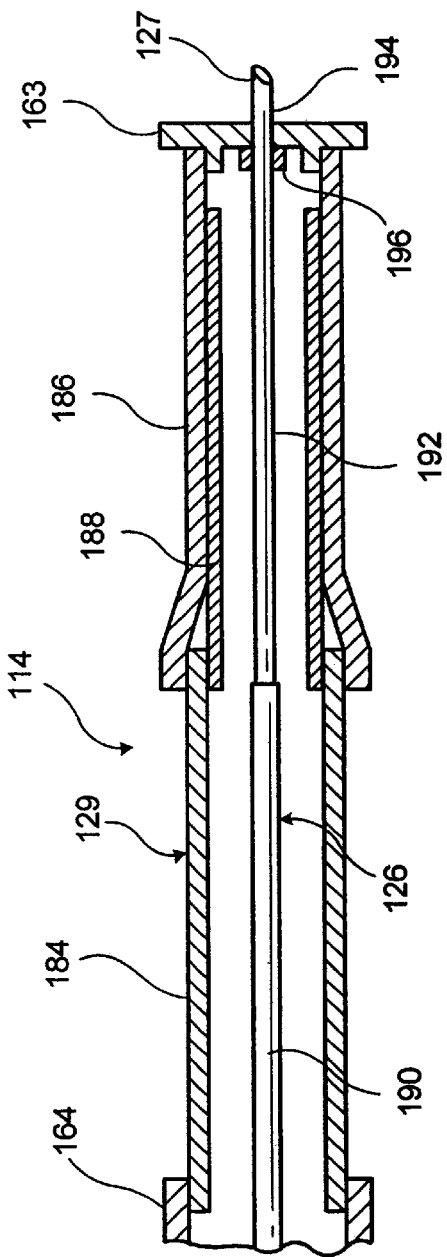
FIG. 12 is an enlarged cross-sectional view of the catheter from FIG. 10.

FIG. 12 is a cross-sectional view of a preferred embodiment of catheter 114 including inner shaft 126 and outer shaft 129. As shown in FIG. 12, outer shaft 129 is connected by suitable heat adhesive to manifold 164. Outer shaft 129 includes a proximal portion 184 which is preferably a co-braided member having, for example, an inner and outer layer of PEBA and a stainless steel reinforcing braid disposed therebetween. Outer shaft 129 also preferably includes a distal portion including a spring coil 188 and an outer polyethylene sheath 186. Connected to the distal end of sheath 186 is hood 163. Hood 163 is preferably formed from an atraumatic material and can include radiopaque material to enhance visibility by fluoroscopy. Inner tube 126 preferably includes a proximal portion 190 which can be formed from, for example, heat treated stainless steel and a distal portion 192 which is preferably formed from a Nitinol hypotube. A needle 194 having a distal tip 127 is preferably attached to the distal portion 192 by a swage collar 196, which may be radiopaque, can engage with hood 163 to limit the distal travel of inner shaft 126 relative to outer shaft 129.

It can be appreciated by those skilled in the art that there are numerous materials which can be advantageously used to construct the apparatus disclosed herein. These materials should be selected in view of the use to which the apparatus are put.

In use, the needle 194 would be coated with a coating and a first agent at any time prior to the insertion of the catheter into the patient's body. Then, once the atraumatic hood 163 was positioned adjacent to the target site, the needle, coated with coating that contained the first agent, would be injected into the target site by pulling the trigger 127 and then allowing the needle to remain within the target site until the agent had been properly deployed. If a second agent needed to be deployed during the procedure the operator would rotate the handle 134 to urge the second agent resident in the inner chamber out the sharpened distal end of the needle 194 while the needle remained in the target site.

Other embodiments than the those described above are also feasible. For example, in a sixth embodiment, rather than leaving the injection structure within the body of a patient for a predetermined amount of time, so that the agent may diffuse from the polymer, the polymer and the agent may, instead, both be left behind in the target site upon the removal of the injection structure from the target site. In this sixth embodiment the polymer and agent would remain behind to further treat the targeted site after an initial amount of agent had been dispensed from the polymer when the injection structure was first inserted into the target site.

Similarly, in a seventh embodiment, the coating and the agent may be released from the injection structure while the injection structure is resident within the target site. In this seventh embodiment the polymer may be released by virtue of a greater affinity for the target site tissue, as in a bioadhesive polymer; alternatively, the polymer may solidify when it comes in contact with the tissue and flake off of the injection structure as with Atrigel (Atrix) and SABRE (Southern Biosystems) polymers.

In an eighth embodiment, the agent released from the orifice of the injection structure may trigger the release of the polymer from the injection structure instead of merely the entry of the injection structure into the body. Moreover, in a ninth embodiment, a sheath may be placed over the coated injection structure to protect the coating and the first agent. The sheath may then dissolve after insertion into the target site, or it may be removed just prior to the insertion of the injection structure into the body or the target site.

Furthermore, in a tenth embodiment, as mentioned above, a second agent may not be needed. In this embodiment, the injection structure would not need to contain an orifice and the delivery device would not need to contain a storage reservoir for the second agent. Lastly, in an eleventh embodiment, rather than deploying the second agent after the injection structure is inserted into the body, the second agent could be combined with the first agent and introduced into the target site with the first agent through the simple insertion of the injection structure into the target site.

In sum, the present invention provides a comprehensive method and apparatus for diagnostic and therapeutic agent delivery. The embodiments conveyed above are illustrative of the various ways in which the present invention may be practiced. Consequently, other embodiments may also be implemented by those skilled in the art without departing from the spirit and scope of the present invention.

What is claimed is:

1. A method for injecting an agent into the body of a patient comprising:
    (a) providing a catheter having a proximal end and a distal end and a rigid injection structure located at the distal end of the catheter, the rigid injection structure having a piercing tip;
    (b) covering the rigid injection structure with a coating, the coating containing a first agent, the first agent retained within the coating until the injection structure is urged into a first target site located in the body of the patient;
    (c) urging the piercing tip of the injection structure into the first target site; and
    (d) maintaining the injection structure in the first target site for a predetermined amount of time, allowing the agent to release from the injection structure into the body.

2. The method of claim 1 further comprising:
    (e) removing the injection structure from the first target site;
    (f) urging the piercing tip of the injection structure into a second target site in the body of the patient; and (g) maintaining the injection structure in the second target site for a predetermined amount of time.

3. The method of claim 1 further comprising:
   (e) injecting a second agent into the first target site through a lumen located in the injection structure.

4. The method of claim 1 wherein the coating deforms in response to an environmental stimulus.

5. The method of claim 1 wherein the first agent is a genetic material.

6. The method of claim 1 wherein the coating releases the first agent in response to an environmental stimulus.

7. A method for injecting an agent into the body of a patient comprising:
   (a) covering an injection structure having a piercing tip with a coating, the coating containing a first agent;
   (b) urging the piercing tip of the injection structure into a first target site;
   (c) maintaining the injection structure in the first target site for a predetermined time;
   (d) removing the injection structure from the body of the patient; and
   (e) treating the coating with the first agent.

8. The method of claim 7 further comprising:
   (g) positioning the injection structure back into the first target site.

9. The method of claim 7 further comprising:
   (g) urging the piercing tip of the injection structure into a second target site in the patient's body.

10. A method for injecting an agent into the body of a patient comprising:
    (a) covering an injection structure having a piercing tip with a coating, the coating containing a first agent;
    (b) urging the piercing tip of the injection structure into a first target site;
    (c) maintaining the injection structure in the first target site for a predetermined time;
    wherein the coating is a swellable porous polymer.

11. A method for injecting an agent into the body of a patient comprising:
    (a) covering an injection structure having a piercing tip with a coating, the coating containing a first agent;
    (b) urging the piercing tip of the injection structure into a first target site;
    (c) maintaining the injection structure in the first target site for a predetermined time;
    wherein the coating is charged to attract oppositely charged therapeutic.

12. A drug delivery device comprising:
    a catheter having a proximate end and a distal end;
    an injection structure having a piercing end, the injection structure located at the distal end of the catheter; and
    a dispensing chamber located within the catheter,
    the injection structure covered with a coating containing an agent,
    the coating adapted to release the agent upon entry into the body.

13. A drug delivery device comprising:
    a catheter having a proximate end and a distal end; and
    an injection structure having a piercing end, the injection structure located at the distal end of the catheter,
    the injection structure covered with a coating containing an agent,
    the coating adapted to release the agent upon entry into the body,
    wherein the coating is adapted to expand after contact with the tissue of a patient for a predetermined amount of time.

* * * * *